United States Patent
Vilsmeier

(10) Patent No.: US 6,724,922 B1
(45) Date of Patent: Apr. 20, 2004

(54) VERIFICATION OF POSITIONS IN CAMERA IMAGES

(75) Inventor: Stefan Vilsmeier, Poing (DE)

(73) Assignee: BrainLAB AG, Heimstettem (DE)

( * ) Notice: Subject to any disclaimer, the term of this patent is extended or adjusted under 35 U.S.C. 154(b) by 0 days.

(21) Appl. No.: 09/422,590

(22) Filed: Oct. 21, 1999

(30) Foreign Application Priority Data

Oct. 22, 1998  (DE) .......................................... 198 48 765

(51) Int. Cl.$^7$ ................................................ G06K 9/00
(52) U.S. Cl. ...................... 382/128; 382/154; 382/291; 348/48; 378/41; 610/310; 610/426
(58) Field of Search ................................. 382/131, 154, 382/291; 348/47, 48; 378/41, 63; 600/310, 426

(56) References Cited

U.S. PATENT DOCUMENTS

| | | | |
|---|---|---|---|
| 3,720,817 A | 3/1973 | Dinwiddie | 235/151.11 |
| 4,118,631 A | 10/1978 | Froggatt | 250/492 R |
| 4,197,855 A | 4/1980 | Lewin | 128/653 |
| 4,341,220 A | 7/1982 | Perry | 128/630 |
| 4,360,028 A | 11/1982 | Barbier et al. | 128/659 |
| 4,583,538 A | 4/1986 | Onik et al. | 128/303 |
| 4,671,256 A | 6/1987 | Lemelson | 128/1.1 |
| 4,791,934 A | 12/1988 | Brunnett | 128/653 |
| 4,849,912 A * | 7/1989 | Leberl et al. | 348/141 |
| 4,945,914 A | 8/1990 | Allen | 128/653 |
| 5,222,499 A | 6/1993 | Allen et al. | 128/653.1 |
| 5,230,338 A | 7/1993 | Allen et al. | 128/653 |
| 5,325,449 A * | 6/1994 | Burt et al. | 382/240 |
| 5,342,054 A * | 8/1994 | Chang et al. | 473/156 |
| 5,394,875 A | 3/1995 | Lewis et al. | 128/660.09 |
| 5,446,548 A * | 8/1995 | Gerig et al. | 250/462.1 |
| 5,590,215 A | 12/1996 | Allen | 382/128 |
| 5,682,890 A | 11/1997 | Kormos et al. | 128/653.2 |
| 5,732,703 A | 3/1998 | Kalfas et al. | 128/653.1 |
| 5,769,789 A | 6/1998 | Wang et al. | 600/414 |
| 5,769,861 A | 6/1998 | Vilsmeier | 606/130 |
| 5,772,594 A | 6/1998 | Barrick | 600/407 |
| 5,796,386 A * | 8/1998 | Lipscomb et al. | 345/156 |
| 5,799,055 A | 8/1998 | Peshkin et al. | 378/42 |
| 5,820,553 A * | 10/1998 | Hughes | 378/65 |
| 5,852,672 A * | 12/1998 | Lu | 356/604 |
| 5,902,239 A | 5/1999 | Buurman | 600/427 |
| 5,940,139 A * | 8/1999 | Smoot | 348/584 |
| 5,967,982 A | 10/1999 | Barnett | 600/429 |
| 5,980,535 A | 11/1999 | Barnett et al. | 606/130 |
| 5,993,194 A * | 11/1999 | Lemelson et al. | 431/14 |
| 5,995,649 A * | 11/1999 | Marugame | 345/419 |
| 5,995,681 A * | 11/1999 | Lee et al. | 356/139.03 |
| 5,999,837 A | 12/1999 | Messner et al. | 600/407 |
| 6,405,072 B1 * | 6/2002 | Cosman | 600/426 |

FOREIGN PATENT DOCUMENTS

WO    WO98/35720    8/1998

OTHER PUBLICATIONS

U.S. application No. 08/919,454, filed Aug. 28, 1997.

* cited by examiner

*Primary Examiner*—Samir Ahmed
*Assistant Examiner*—Anand Bhatnagar
(74) *Attorney, Agent, or Firm*—Renner, Otto, Boisselle & Sklar, LLP

(57) ABSTRACT

The invention concerns a method for showing three-dimensionally defined fiducial points in a video camera image involving monitoring of a spatial region by at least two cameras which can map invisible light, especially infrared light, and by at least one video camera, computer-assisted analysis of the image data of the cameras, using the three-dimensional data obtained by means of the invisible-light cameras to compute the spatial location of objects located in the monitored spatial region as mapped by the invisible-light cameras, and displaying the fiducial points assigned to the objects together with the video image; the invention also relating to an apparatus for implementing the method or for visually verifying the correct position of an object.

14 Claims, 1 Drawing Sheet

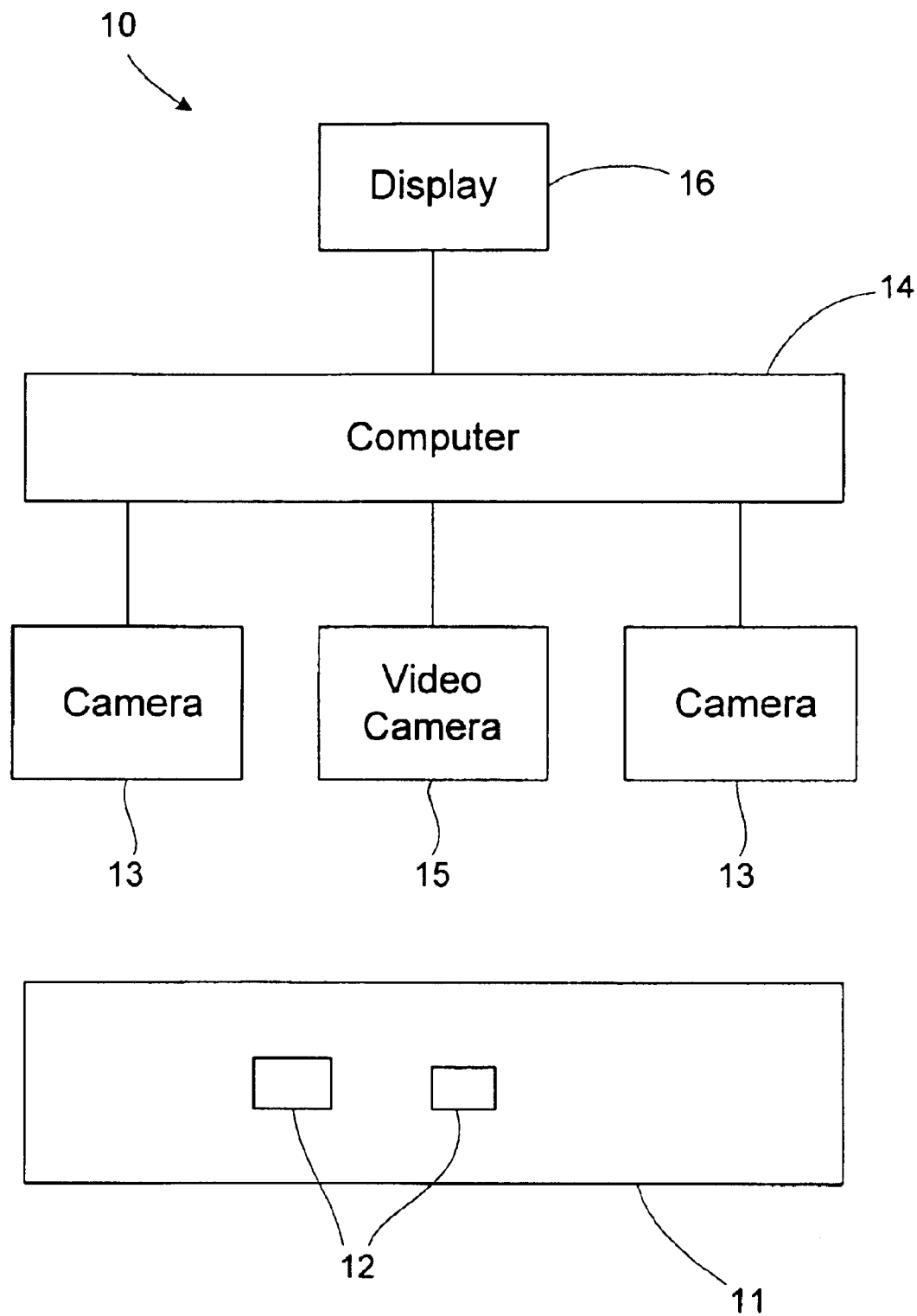

VERIFICATION OF POSITIONS IN CAMERA IMAGES

BACKGROUND OF THE INVENTION

1. Field of the Invention

The present invention concerns a method for showing three-dimensionally defined fiducial points in a video camera image, it relating more particularly to a method of visually verifying the correct position of an object and, especially, to a method of visually verifying the correct position of a patient in surgery. The invention concerns furthermore an apparatus for implementing such methods or for visually verifying the correct position of an object.

2. Description of Prior Art

In particular, in the field of medicine for quite some time one has turned to providing systems which optically assist localizing or positioning of patients, of body parts requiring treatment, or of instruments in the operating room with the aid of a computer.

Conventionally, e.g. in radiotherapy, the position of a tumor as displayed in an x-ray image, or images of another imaging method, is marked by tinting the skin of the patient before aiming the radiation beam at this position and then activating radiation.

Since these methods are hampered by being very inaccurate and fail to meet the accuracy with which radiotherapy/surgery is nowadays possible, systems have been developed which provide computer-assisted precise positioning.

For example, patient landmarks are applied to the surgical target site so that the position of the target volume relative to the landmarks can be precisely mapped by means of a CT scan and saved in a data record. Then, when the patient is brought into the radiosurgical unit, the position of the landmarks can be mapped three-dimensionally by a navigation system, comprising, for instance, two infrared cameras connected to a computer, and the position of the lesion targeted in the operating room can be determined with the aid of the data record from the CT scan. As soon as the spatial location of the focal point of the radiosurgical unit is made known to the computer, the target volume can be precisely brought to this focal point with the aid of this data for then implementing exact target radiosurgery.

Precise positioning in this way is, of course, just as applicable in any other technical application requiring the exact location of an object.

Problems exist, however, in this approach due to no verification mechanism whatsoever being available. In other words, for example, once the patient has been positioned as explained above, the radiosurgeon has to place absolute faith in the system when he switches the radiosurgical unit on, since he no longer has any means of making a visual check with adequate precision and is unable to establish whether malpositioning might have taken place, for instance, due to a glitch in the system.

SUMMARY OF THE INVENTION

It is thus the object of the present invention to provide a method and apparatus permitting verification of computer-assisted positioning procedures as discussed above.

This object is achieved in accordance with the invention by a method for showing three-dimensionally defined fiducial points in a video camera image including:

monitoring a spatial region by at least two cameras which can map invisible light, especially infrared light, and by at least one video camera;

computer-assisted analysis of the image data of the cameras using the three dimensional data obtained by means of the invisible-light cameras to compute the spatial location of objects located in the monitored spatial region and mapped by the invisible-light cameras; and outputting on to a display the fiducial points assigned to the objects together with the video image.

The advantage of the method in accordance with the invention is basically that visual verification is now made possible. When objects are brought into the spatial region monitored by the cameras they are mapped, on the one hand, by the video camera and, on the other, by the two other invisible-light cameras, and following analysis and assignment of the data it is visible from the display whether the fiducial points coincide with the video image points of the objects. If this is the case, then it can be safely assumed that the computer-assisted positioning was successful, whereas if there is a discrepancy, the positioning needs to be corrected or repeated.

The special advantage in using invisible-light cameras, i.e. particularly infrared light cameras, is that mapping the position three-dimensionally may be done with no interference from visible light irradiation or reflections and can thus be implemented with enhanced accuracy and less computation.

In one special embodiment, the method in accordance with the invention for showing three-dimensionally defined fiducial points in a video camera image comprises the following steps:

monitoring a spatial region by at least two cameras which can map invisible light, especially infrared light, and by at least one video cameras monitoring an essentially identical spatial region by at least one video camera;

computer-assisted analysis of the image data of the cameras;

introducing a calibration tool comprising landmarks, capable of being mapped by both the invisible-light cameras and by the video camera, into the spatial region monitored by the cameras;

computer-assisted assignment of the spatial location of the landmarks on the calibration tool in the video camera image by means of the three-dimensional data obtained by the invisible-light cameras relative to the position of landmarks on the calibration tool;

computing, on the basis of this assignment, the spatial coordinates of objects introduced into the monitored spatial region and mapped by the invisible-light cameras, said coordinates being then outputted on a display as fiducial points together with the video image.

It is this calibration that informs the system how the spatial regions monitored by the video camera, on the one hand, and by the invisible-light cameras, on the other, relate to each other positionally, the computer also being informed of how the positions change when known three-dimensional objects in the monitored spatial region move and enabling it to subsequently assign the three-dimensional structures positionally in the video image.

In accordance with one preferred embodiment of the invention, the calibration tool, whose landmark array is saved in the computer, is moved in the monitored spatial region until an output (e.g. a sound output) occurs computer-assisted, indicating conclusion of the calibration. The operator then knows that the video image is calibrated and is now able to implement the actions assisted by the system.

As already mentioned, preferably two infrared cameras and a video camera are used. These cameras are arranged preferably so that the two infrared cameras monitor the spatial region from two outer points while the position of the video camera is essentially uncritical, it being arranged in one embodiment at a point located roughly on the centerline between the two other cameras. Using ultraviolet cameras is also principally conceivable.

In accordance with one proposed application of the method in accordance with the invention, the monitored spatial region is an operating room, especially a radiotherapeutical or radiosurgical operating room. The objects displayed in the video image for the fiducial points may be patient landmarks in this special application. This is where application of the method in accordance with the invention comes in useful for medical purposes, especially in radiosurgery, where it is of vital importance to verify that the beam focus is targeted on the part of the body to receive radiation, i.e. the tissue lesion. The radiosurgeon can check in the video image for agreement of the fiducial points with the landmarks on the patient before undertaking radiosurgery.

There is also the possibility of displaying—in addition to the objects for which fiducial points are displayed in the video image—further information for objects in the video image. More particularly, patient body parts or the contours thereof may be rendered visible, the arrangement of which relative to the fiducial points is known. If put to use in radiosurgery, when, for example, data as to the positions of the organs relative to the patient landmarks is available from a computerized tomography (CT), the video image can be superimposed by a type of "glass" image of the patient displaying the organs, and especially the parts of the organ to undergo surgery, in the correct spatial position and with contours diminished in size behind, i.e. as if one could actually see into the patient. If, for example, the patient is required to undergo radiation treatment at a point in the left lung, the surgeon is now also able to compare whether the target lines of a radiosurgical unit, displayed by means of laser lines, actually do locate the focal point on the diseased tissue target site.

In one general embodiment of the invention, a method is made available for visually verifying the correct position of an object by applying landmarks to the object and mapping the position of an object part relative to the landmarks and analyzing or saving the results computer-assisted;

bringing the object with the landmarks into a monitoring room and establishing, by means of a method as discussed above, the correct position of the object or object part when all or a representative number of landmarks appear in the video image at the positions at which the fiducial points are displayed or superimposed.

In one special embodiment, the method as lastly mentioned can serve to visually verify the correct position of a patient by applying patient landmarks to the patient and mapping the position of a body part requiring surgery relative to the patient landmarks and analyzing or saving the results computer-assisted;

bringing the patient with the patient landmarks into an operating room and establishing, by means of a method as discussed above, the correct position of the patient or body part requiring surgery when all or a representative number of patient landmarks appear in the video image at the positions at which the fiducial points are displayed or superimposed.

Here too, of course, there is the possibility of displaying, in addition to the fiducial points, organ structures or target volumes in the video image.

As mentioned at the outset, and with reference to the sole figure, the invention also provides an apparatus 10 for visually verifying the correct position of an object 12, comprising landmarks 12 for applying to the object;

at least two cameras 13 which map invisible light, especially infrared light, for monitoring a spatial region in which the object is located; and a computer 14 which maps and analyzes the position of the object or an object part relative to the landmarks by means of image data of the invisible-light cameras computer-assisted.

To achieve the object of the invention, likewise cited at the outset and with continued reference to the sole figure, the apparatus in accordance with the invention comprises at least one video camera 15 monitoring essentially the same spatial region; and a computer-assisted display output for the image of the video camera on which the spatial coordinates of the object, mapped by the cameras for invisible light and computed or analyzed by the computer, are output on a display 16 as assigned fiducial points or structures together with the video image.

Using this apparatus, the method in accordance with the invention can be advantageously implemented and achieve the advantages already cited above. It will be appreciated that, of course, all of the aforementioned features in conjunction with medical, especially radiotechnical, applications are achievable with the apparatus in accordance with the invention as advantageous embodiments.

In one preferred embodiment of the apparatus in accordance with the invention, the landmarks are reflectors for invisible light, more particularly infrared light, and a source of invisible radiation is provided to illuminate the spatial region. This contributes towards uncomplicated handling of the apparatus.

What is claimed is:

1. A method for providing visual verification of mapped fiducial points on an object with the actual position of the fiducial points in a video image of the object, comprising:

monitoring a spatial region including the object by at least two cameras which can map invisible light;

monitoring the spatial region by at least one video camera that produces a video image of the spatial region including the object and in which the fiducial points on the object are visible;

computing the spatial location of the fiducial points on the object in said monitored spatial region as mapped by said invisible-light cameras; and showing in overlapping relationship on a display the video image in which the fiducial points on the object are visible and also the fiducial points at their computed spatial locations in the same frame of reference as the video image shown on the display, thereby to enable visual verification of the computed spatial locations of the fiducial points with the positions of the fiducial points in the video image shown on the display.

2. The method of claim 1, comprising introducing a calibration tool comprising landmarks, capable of being mapped by both said invisible-light cameras and by said video camera, into the spatial region monitored by said cameras;

computer-assisted assignment, by means of the three-dimensional data obtained by said invisible-light cameras, of the spatial location of said landmarks on said calibration tool in said video camera image relative to said position of landmarks on said calibration tool, thereby to establish a means by which fiducial points on the object can be related to spatial locations in the same frame of reference as the video image shown on the display; and computing, on the basis of the computer-assisted assignment, the spatial coordinates of the fiducial points mapped by said invisible-light cameras in the said frame of reference and outputting said coordinates as fiducial points together with said video image on a display.

3. The method as set forth in claim 2, wherein two infrared cameras are used as the invisible-light cameras.

4. The method as set forth in claim 2, wherein said calibration tool, whose landmark array is memorized in said computer, is moved in said monitored spatial region until an output occurs computer-assisted indicating conclusion of calibration.

5. The method as set forth in claim 1, wherein said monitored spatial region is within an operating room.

6. The method as set forth in claim 1, wherein said fiducial points are patient landmarks.

7. The method as set forth in claim 1, wherein further object data is shown on the display along with said video image and the fiducial points at their computed spatial locations.

8. The method as set forth in claim 7, wherein said further object data includes parts of the body of a patient and/or contours and/or target volume of the patient for radiotherapy/surgery.

9. The method as set forth in claim 1, comprising applying the landmarks to the object.

10. The method as set forth in claim 1, further comprising the landmarks.

11. The method as set forth in claim 1, wherein said monitored spatial region is within a radiotherapeutical or radiosurgical operating room.

12. An apparatus for visually verifying mapped fiducial points on an object with the actual position of the fiducial points in a video image of the object, comprising:

at least two cameras which map invisible light, for monitoring a spatial region in which said object is located; and at least one video camera monitoring the spatial region, for producing a video image of the spatial region including the object and in which the fiducial points on the object are visible;

a computer for computer-assisted mapping, by use of the invisible-light cameras, of the spatial location of the fiducial points on the object in said monitored spatial region into the same frame of reference as the video image when shown on a display; and a display for showing in overlapping relationship the image of the video camera in which the fiducial points are visible and also the fiducial points at their computed spatial locations in the same frame of reference as the video image shown on the display, thereby to enable visual verification of the computed spatial locations of the fiducial points with the positions for the fiducial points in the video image shown on the display.

13. The apparatus as set forth in claim 12, further comprising the landmarks and a source of invisible light for illuminating said landmarks, and wherein said landmarks are reflectors that reflect the invisible light.

14. The apparatus as set forth in claim 12, wherein the invisible light cameras are infrared cameras.

* * * * *